United States Patent [19]

Hennessy et al.

[11] 4,042,808
[45] Aug. 16, 1977

[54] PARTICLE COUNT CORRECTION

[75] Inventors: James W. Hennessy; Henry R. Angel, both of Trumbull; Bernard O. Bachenheimer, Fairfield, all of Conn.

[73] Assignee: Angel Engineering Corporation, Stratford, Conn.

[21] Appl. No.: 603,586

[22] Filed: Aug. 11, 1975

[51] Int. Cl.² .................................... G06M 11/00
[52] U.S. Cl. .......................... 235/92 PC; 235/92 PL; 235/92 CC; 235/92 R
[58] Field of Search ......... 235/92 PC, 92 CC, 92 PL; 324/71 CP

[56] References Cited

U.S. PATENT DOCUMENTS

| | | | |
|---|---|---|---|
| 3,209,130 | 9/1965 | Schmidt | 235/92 PL |
| 3,648,030 | 3/1972 | Sheperd et al. | 235/92 PL |
| 3,737,633 | 6/1973 | Collineau | 235/92 PL |
| 3,864,551 | 2/1975 | Oefinger | 235/92 PL |

Primary Examiner—Joseph M. Thesz
Attorney, Agent, or Firm—Robert P. Cogan; Timothy L. Burgess

[57] ABSTRACT

A method and apparatus for correcting the output count of an electronic particle counting system in which additional correction pulses are added to the pulses generated by the electronic counting system as a result of detecting particles flowing through an orifice. The correction pulses are added in accordance with a curve which is generated by statistical computation determined by the size of the orifice and the character of the particles being detected therein and their quantity per unit volume. The improved apparatus comprises the addition of a second counter chain to the system which includes digital counters having outputs at various frequencies which are dividends of the frequency of the input pulses. The various-frequency outputs are combined through logic circuitry to generate individual correction pulses at frequencies such that when the pulses are added to the detected pulses, the total of the pulses corresponds to the actual number of particles flowing through the orifice.

16 Claims, 6 Drawing Figures

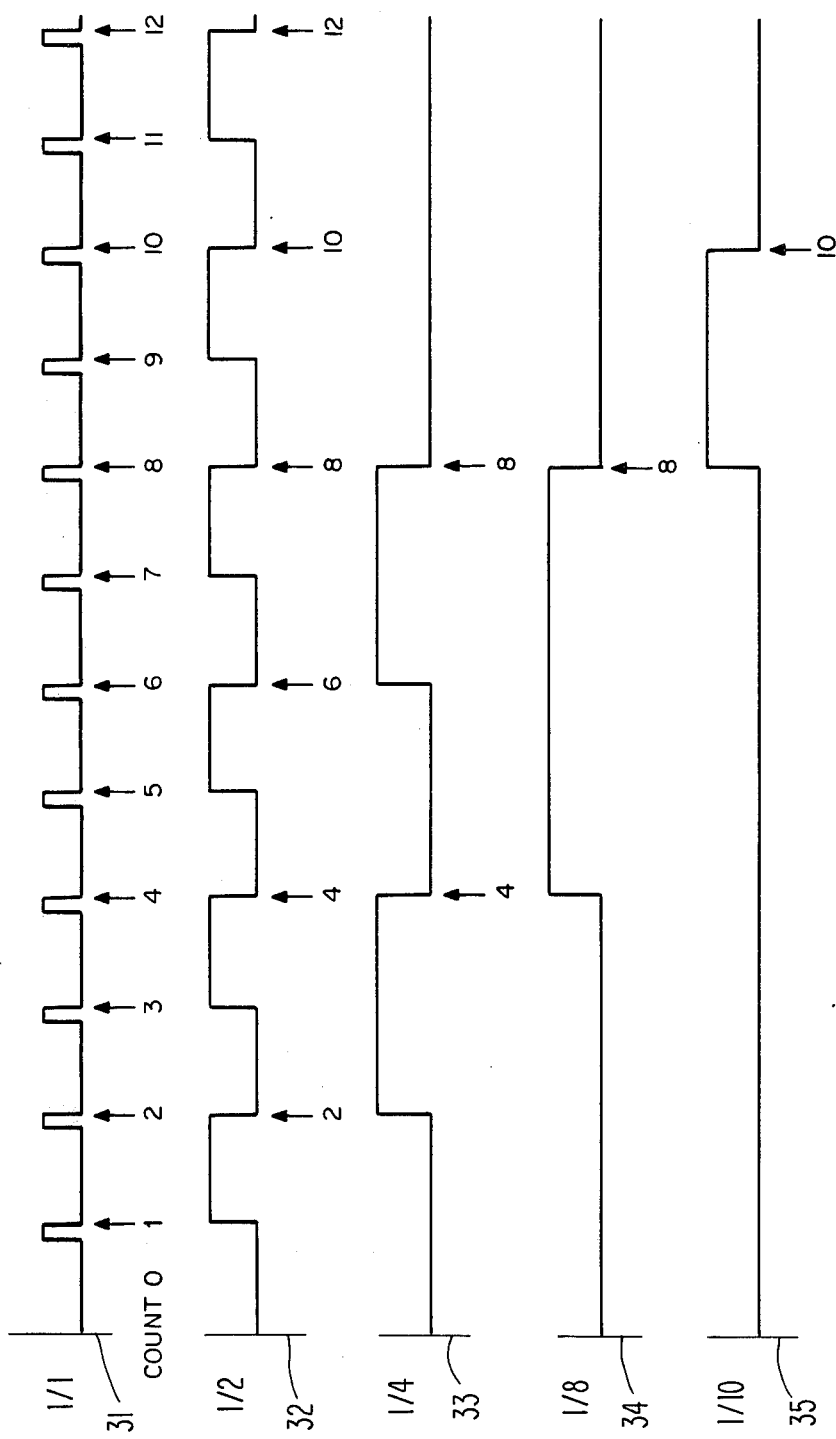

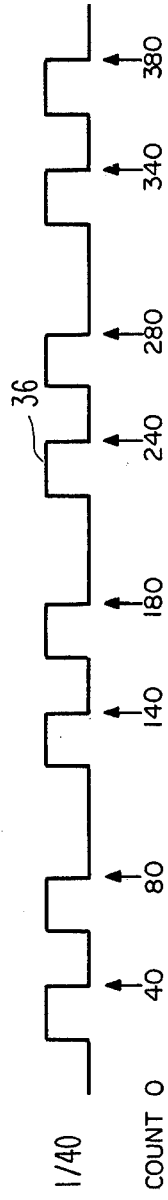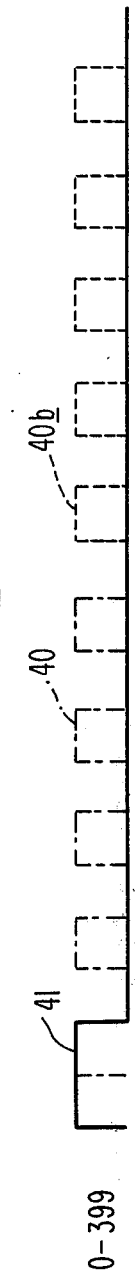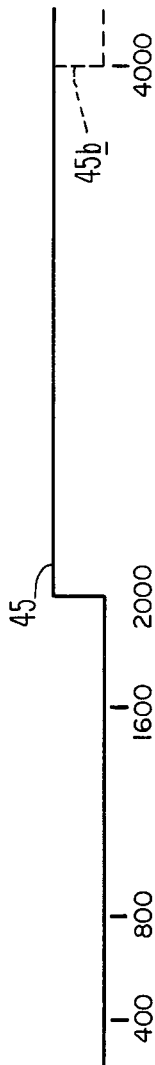

PARTICLE COUNT CORRECTION

The present invention relates to particle counters in which the concentration of particles in a solution is determined by passing a predetermined volume of the solution and counting the particles electronically as they pass through thr orifice. The present invention has particular application to a blood test device shown in copending application of Angel et al., Ser. No. 445,123, now U.S. Pat. No. 3,921,066 issued Nov. 18, 1975.

BACKGROUND OF THE INVENTION

Particle counters of the stated type are commonly used to determine the biological and hematological cell counts as well as various industrial particle counting uses. Such counters rely on electronically-generated pulses generated by the passage of a particle through the orifice, which pulses are counted electronically and displayed or otherwise read by the test apparatus. As the density of the particles in the fluid carrier increases, the probability of particles being coincident during the detection in the orifice increases, resulting in a reduced count when compared to the actual number of particles passing through the orifice. For a given orifice, and for a given character of particle, the number of such coincident particles may be statistically determined for a specific density of particles per unit volume of solution and conversion parameters may be provided for translating the electronic count to an actual count, without the necessity for further diluting the sample so as to reduce the density of the particles in the sample and thereby the likelihood of particles passing through in coincidence.

Prior to the present invention, coincidence correction has been accomplished by providing correction tables for the readings generated by the electronic count which the operator may use to convert the electronic count to the actual count. Such a procedure is time consuming and introduces a risk of human error. A proposal for electronically storing the correction tables and correcting the digital output by the stored data, as described in U.S. Pat. No. 3,864,551, was found to be uneconomical. Another means of providing coincidence correction is to simply provide an analog read-out and provide a correction in the scale of the analog read-out meter. However, the inaccuracies inherent in an analog read-out are undesirable.

An electronic correction is disclosed in U.S. Pat. No. 3,626,164 wherein electronic circuitry is provided to periodically feed correction signals to the counter in accordance with a schedule determined by the statistical probability of coincidence related to the cumulative total in the counter, so that a corrected count may be read from the digital counter. The intermittent correction of this patented counter requires the addition of a multitude of pulses at spaced intervals of correction which affects the accuracy of the corrected count variably according to the interval between the corrections.

With the foregoing in mind, the present invention makes use of the well-known principles and readily available components to provide a single-increment correction at periodic intervals, the length of the intervals between corrections being modified as the statistical data requires a different degree of correction.

In a preferred embodiment of the invention, the correction is accomplished by the use of two counters, one to record the count of the detected particles with the coincidence correction pulses added to it so that it may be used with a digital display to show the true particle count or with other read-out devices. A second counter is used to receive the actual detected count and to control the addition of correction pulses to the detected count fed to the first counter as the count progresses. The second counter therefore provides a correction pulse at the predetermined intervals by using the same counter, both as a pulse generating means and as a timing means.

The invention will now be described in greater detail with reference to the accompanying drawings illustrating a preferred embodiment of the invention, wherein.

Figure 1:
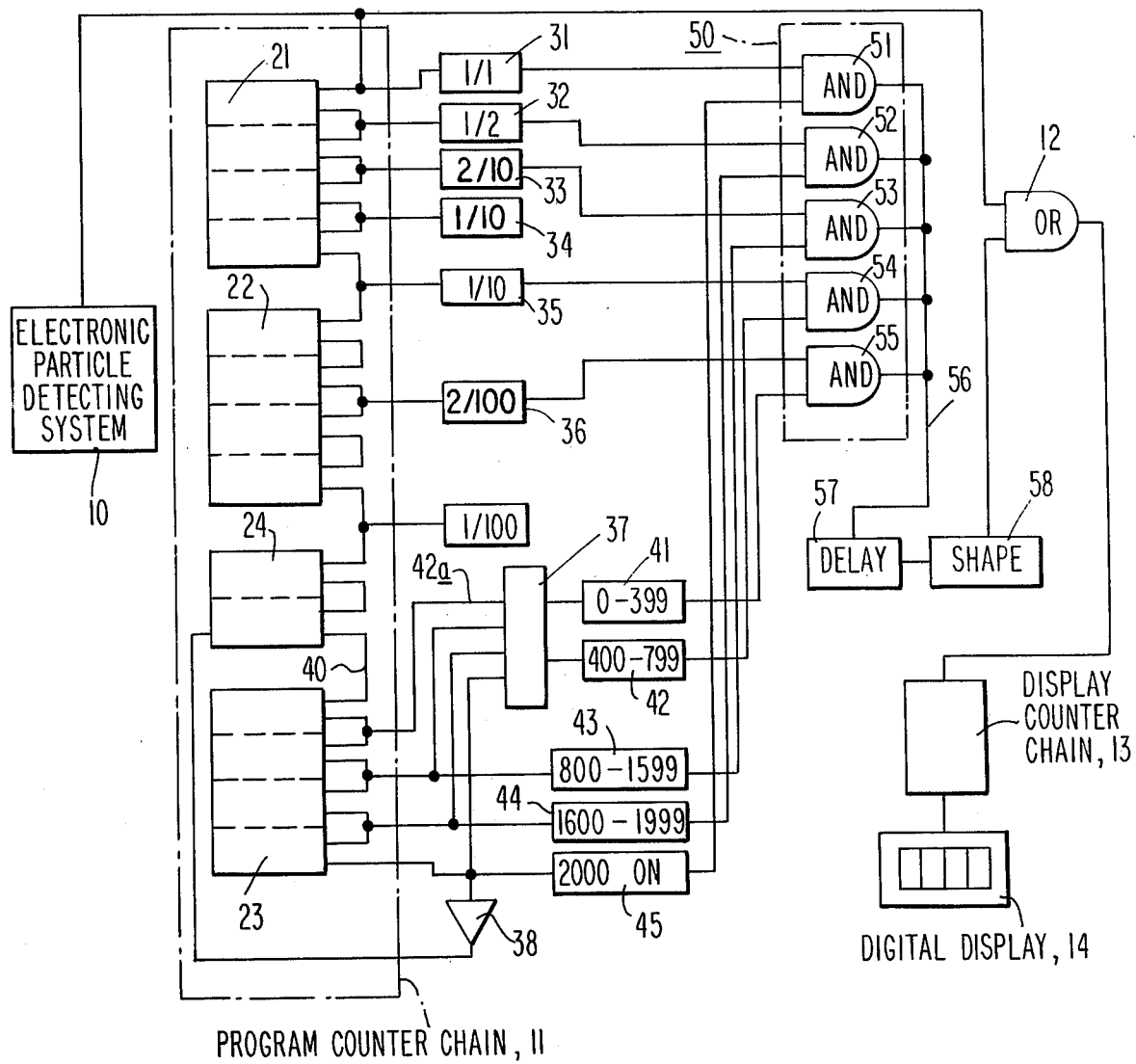
FIG. 1 is a block diagram of apparatus including a particle detecting and counting system embodying particle count correction in accordance with the present invention.
Figure 1A:
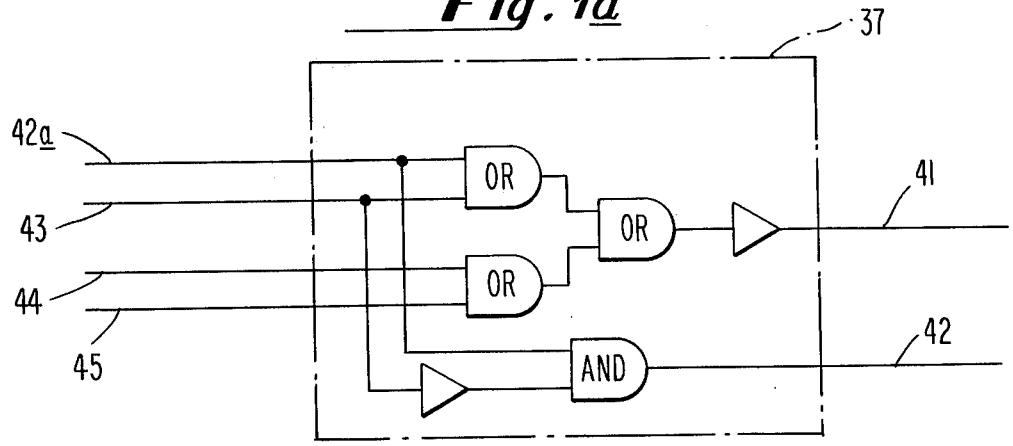
FIG. 1a is a schematic of the elements in block 37 of FIG. 1.
Figure 3:
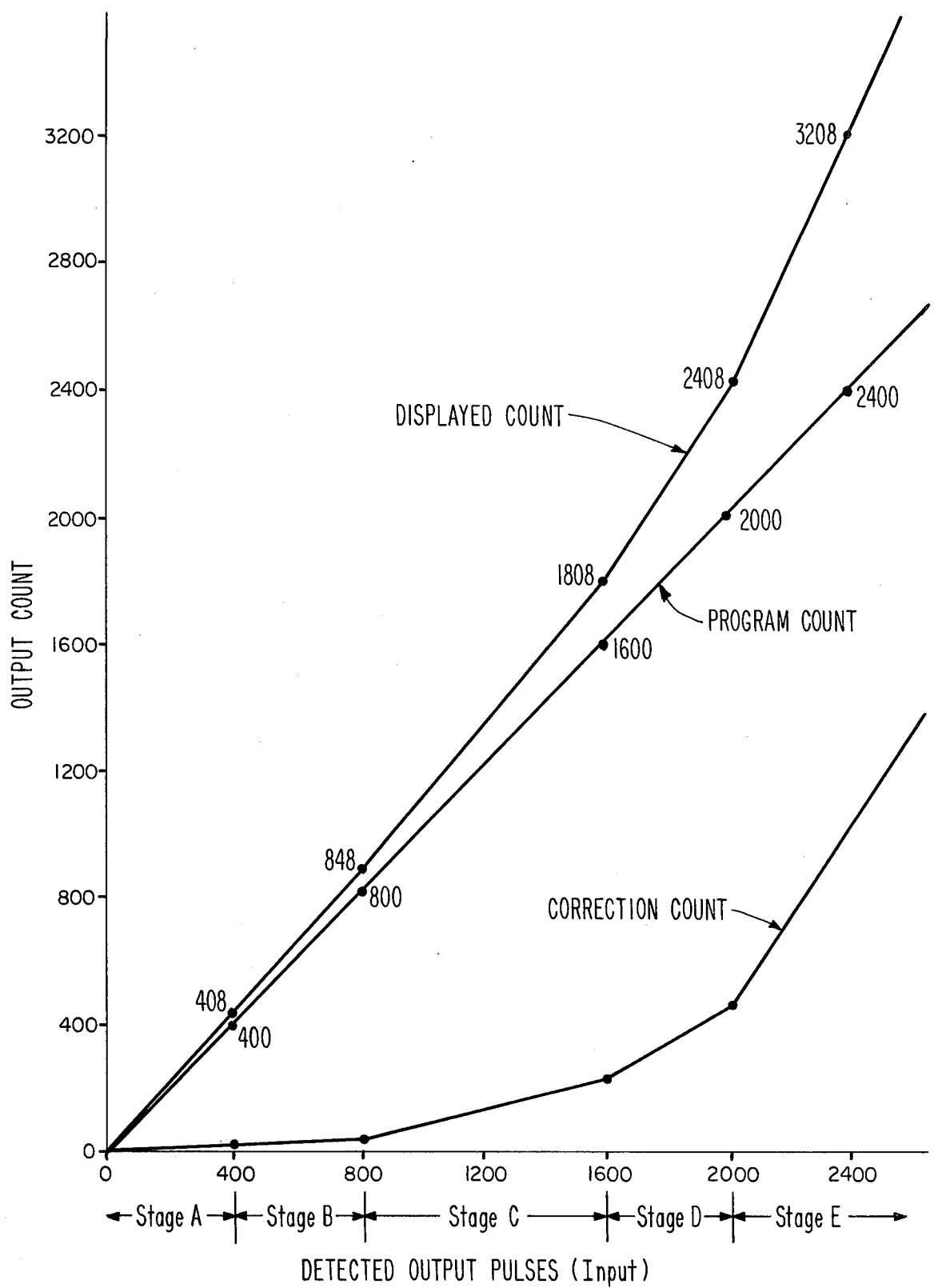

FIG. 2a plots the digital voltage output against time for each of the outputs of the second counter in a counter chain illustrated in FIG. 1;

FIG. 2b similarly plots digital voltage output against time on a different scale for a longer interval output of a second counter;

FIG. 2c similarly plots digital voltage output against time on a different time scale for outputs still further along in the counter chain; and FIG. 3 shows the digital output counts from the program counter chain and the display counter chain, respectively, plotted against one another, illustrating the correction provided by the apparatus illustrated in the block diagram of FIG. 1.

Referring now to the drawing, and particularly FIG. 1, the diagram illustrates at the lefthand side an electronic particle detecting system 10, in the present instance a system of the type shown in the patent identified above. Reference may be had to the patent for the details of the construction and operation of the counting system, but it is sufficient to state that the system has an output consisting of a sequence of counting pulses which is determined by the number of particles passing through the orifice of the system as a predetermined volume of the test solution is passed through the orifice. The pulses issuing from the particles detecting system 10 may be of the digital configuration 31 shown in the 1/1 line of FIG. 2a. As the frequency of particles passing through the orifice may vary, the pulse duration of the pulses shown in FIG. 2a, in practice, may not be uniform. Neither frequency nor pulse width need be uniform, since the counter system responds to the negative-going pulse edge as indicated by the arrows in FIGS. 2a and 2b.

Referring back to FIG. 1, the output pulses or signals from the particle detecting system 10 are fed into a program counting chain 11 and are also fed into OR gating means 12 leading to a display counter chain 13 which registers on a digital display 14, the pulses being fed to the counter chain 13 by the gating means 12. The display counter chain 13 and digital display 14 are described in greater detail in the aforementioned patent.

The program counter chain 11 includes a plurality of binary-coded decimal counters, in the present instance three, 21, 22 and 23, and a dual flip-flop 24 which are series interconnected in such fashion as to provide digital voltages at varying frequencies, as seen in FIGS. 2a and 2b and 2c, which are dividends of the input pulse frequency, in the selected ratios indicated. The input pulse frequency 31 applied directly is one pulse for each output pulse from the particle detecting system 10. The first output 32 of counter 21 provides one output pulse for every two input pulses, as indicated in FIG. 2a. The next output, 33 of counter 21, provides two pulses for every ten inputs, occurring at count numbers four and eight. A third output, 34 of counter 21, which is the present instance, is not used externally of the counter, provides one pulse for every ten input pulses on the eight-phase count. This is shown only to clarify the binary-coded decimal operation of the counter. A decimal output 35 of counter 21 provides on pulse for every ten pulses on the tenth count. The second binary-coded decimal counter 22 has only a single output 36 (FIG. 2b) used externally. Output 36 provides two pulses for every 100 pulses of the input 31, these pulses occurring with input pulse count numbers 40, 80, 140, 180, 240, etc., as indicated. Outputs 31, 32, 33, 35 and 36 as referred to hereafter as a first group of outputs.

The counter 22 also provides a decimal output every 100 pulses. In between the 100-count decimal ouput of the counter 22 and the input of counter 23 is a two-stage series-connected flip-flop 24. Dual flip-flop 24 has the effect at its output 40 of dividing the 100-count applied at its input by 4 and therefore changes state every 400 counts. The counter 23 has four outputs, 42a, 43, 44 and 45, respectively, which divided by two, four, five and ten, as indicated by the digital voltages in FIG. 2c. These outputs are coupled through suitable gating circuits indicated at 37 to provide output signals 41 and 42 which are grouped with outputs 43, 44 and 45 to constitute a second group of outputs. Furthermore, the output signal 45 from the final stage of the counter 23 is fed back to the "preset" terminal of the flip-flop 24 through an inverter 38. This signal suppresses further changes of state in the flip-flop 24 and therefore interrupts further input to the counter 23.

The gating or switching circuit 37 provides an output signal 41 which is "on" at the start of the input count 31 and is changed state or suppressed when count number 400 is reached, as shown in FIG. 2c. In the present case, the counter outputs 42a, 43, 44 and 45, which switch sequentially, are connected to the circuit 37 to generate the output signal shown at 41. In the circuit 37, an output 42 is "on" from count numbers 400 to 799, as also shown in FIG. 2c. This output is turned off by the output 43 at 800 through the circuit 37. The output 43 is "on" from 800 to 1599 and is cut off thereafter. The output 44 is "on" from 1600 to 1999 and is cut off thereafter, as in FIG. 2c. The output 45 is turned "on" at 2000 and stays "on" thereafter while the signals 41–44 remain "off" until the entire system is reset. In FIG. 2c, the actual input signals to the counter 23 are shown in dot-and-dash lines at 40 and the counter outputs are shown in broken lines 42a and full lines 43, 44 and 45. For purposes of explanation, dotted-line extensions of these signals are shown at 40b, 42b, 43b, 44b and 45b to show the signal outputs which would occur if the flip-flop 24 were not locked up at count 2000.

These particular outputs are selected to enabled programming of the correction circuitry to produce correction pulses in the desired sequence under the control of the input pulses indicated at 31. It should be noted that in this arrangement, the first group of outputs 31 through 36 inclusive is used to generate pulses at their negative-going wave fronts, whereas the second group of outputs 41 through 45 is used as gate signals to select the desired frequency at which to add correction pulses. Only one of these gate signals 41 through 45 is activated at a time thereby permitting only one of the programmed correction frequencies.

The outputs are coupled through gating means generally designated 50, in the present instance a series of AND gates 51, 52, 53, 54 and 55, whose outputs are connected by an OR means 56 to a delay circuit 57 and a pulse-shaping "one shot" multi-vibrator 58 which operates to feed a pulse of the desired shape to the OR gate means 12.

The outputs are coupled in the gating means 50 so that one of the outputs from the first group is coupled with one of the outputs from the second group in each of the gates 51, 52, 53, 54 and 55. Specifically, the output 31 (which corresponds to the input from the particles detecting system 10) is coupled with the output 45 through the gate 51 so that the one-for-one pulses from output 31 are gated through gate 51 when the counter chain has registered 2000 pulses and thereafter. The gate 52 is turned by the output 44 to pass pulses originating from the output 32 when 1600 pulses are registered and is turned off after 1999 pulses are registered. The gate 53 is turned on to the two-for-ten output 33 by gating output 43 when 800 pulses have been registered in the counter chain 11 and turned off after 1599 pulses have been registered. Gate 54 passes the signal on output 35 to generate one pulse for every ten inputs when the output 42 is positive for counts of 400 through 799. Gate 55 passes the signal on output 36 to generate two pulses for every 100 counted from the start through count 399 when output 41 is positive.

The particular apparatus shown in FIG. 1 is designed to cause the correction curve of FIG. 3 to correspond closely to the correction data derived statistically by calculation from the orifice size, the character of the particles and their density in solution in the particle detecting system 10. It should be noted that the statistical computations will provide a curve with a continuously changing slope. However, in accordance with the present invention, the correction curve provided by the method and apparatus of the present invention produces a correction factor comprising a series of straight-line segments, each segment being of constant slope throughout its length and successive sections increasing in slope. The dividing line between adjacent sections in the curve of FIG. 3 are selected to coincide with binary outputs readily obtained from the counter chain 11. Where the correction factor does not follow the simple curve provided by the segments shown in FIG. 3, the outputs of the counter may be combined to provide any desired correction factor in successive stages of the count. The illustrated apparatus provides five different slopes in the correction curve and if additional slopes were found desirable, additional gating means may be added.

When in operation, the gating means 55 puts out a correction pulse from the output 36 every 40 counts of the input 31 during each 100-count cycle. Thus, the OR wire 56 passes the pulse generating negative-going pulse edge to the delay circuit 57 at count number 40 and count number 80 out of each 100 counts. The one shot 58 forms the pulse after a predetermined delay from this edge of the delay circuit. Therefore, when the delayed pulse is fed to the gate 12, it does not coincide with the input pulse from the particle detecting system 10, which triggered the pulse and is thereby counted by the counter chain 13 as an additional pulse. Thus, in continuous counting, the display 14 shows one count for each of the first forty particles sensed in the particle detecting system 10, and immediately after the fortieth particle count, it adds an additional count. This addition compensates for coincidence in the orifice. Similarly, a second pulse is added after the count eighty so that count eighty-one would be immediately followed by count eight-two on the display 14.

When gating means 54 is in operation starting at count 400, every 10th count would be followed by an additional count so that at the end of 800 particle counts, the display shows 848.

When the gating means 53 is in operation, additional counts are added every fourth and eighth count in each ten, so that at the end of the second stage, the 1600 particle counts provide a display of 1808. This is clearly illustrated in the curve shown in FIG. 3, and it is apparent that the straight-line segments may be modified to provide the desired curvature in the correction curve. It is also apparent that the displayed count need not be a continuously increasing output but may be shaped according to the correction desired.

In the foregoing manner, the correction of the digital display is made by a single digit increment so that regardless of the count, the digital display is well within the tolerance capability of the apparatus.

While the present invention has been described in its particular application of the blood test device shown in the copending application identified above, it is apparent that the invention has wide application to electronic particle counters. It has particular application to counters having a digital display, although it may be desirable to incorporate a counter correction embodying the present invention in counters having an analog display, particularly in those cases where the orifice or the character of the particles being counted may be changed and may require an alteration in the configuration of the correction curve. In such cases, it may be desirable to provide switching circuits in association with the various outputs from the program counter chain in order to permit ready change from one curve configuration to another.

While a particular embodiment has been illustrated and described and modifications have been suggested, it is not intended to limit the invention to such disclosure, but changes and modifications may be therein and thereto within the scope of the following claims.

We claim:

1. In apparatus for counting, said apparatus having detector means to emit a pulse for each detection, thereby generating a sequence of counting pulses, said apparatus having a display counter device for providing a read-out of the pulses generated by the detector means; the improvement comprising means to correct the count to compensate for errors introduced by the mode of detection and recording, comprising a program counting device, means to feed said counting pulses into the input of said program counting device, said program counting device having a plurality of output means, one group of said output means each providing a train of pulses at different frequencies, a second group of said output means each for providing in sequence a gating signal during an interval spanning selected numbers of said counting pulses, gate means responsive to application of a gating signal from said second group of output means to transmit a train of pulses from said first group of output means to produce correction signals at a frequency which varies in accordance with a pre-selected program controlled by said second group of said output means, and adding means to add the pulses from said gate means to the sequence of counting pulses from said detector means to generate a corrected count which is read out in said display counter device.

2. Apparatus according to claim 1 wherein said gate means includes a series of individual gate elements, each element being connected to one output means of each of said two groups, the outputs of said gate elements being connected to said adding means, said adding means including an element to shape the correction signals from said gate means into individual correction pulses similar to the pulses in said sequence of counting pulses, and a delay circuit to avoid pulse coincidence so that individual correction pulses may be added to said sequence of counting pulses in intervals between the counting pulses in said sequence.

3. Apparatus according to claim 2 wherein said program counting device includes switching circuitry connected to said second group of said outputs to provide gating voltage levels which operate in sequence to turn on the individual gate elements of said gate means.

4. Apparatus according to claim 1 including means to stabilize and maintain the gating voltage level at a final output of said second group when the input count to said program counting device reaches a selected count.

5. Apparatus according to claim 1 wherein said counter device comprises a digital display according to a digital read-out of the correct count.

6. Apparatus according to claim 1 wherein said program counting device comprises a counter chain responsive to negative-going pulse edges to generate digital output signals.

7. In apparatus for counting particles in which the particles are caused to flow through an orifice, said apparatus having detector means to sense the particles flowing through the orifice and emit a pulse for each such sensed particle, thereby generating a sequence of counting pulses indicative of the number of particles, said particle counter having a counter device for providing a total of the pulses generated by the particle counter; the improvement comprising means to correct the particle count to compensate for errors introduced by the mode of detection and recording of the particles, comprising a second counter device means to feed said pulses into the input of said second counter device, said second counter device having a plurality of output means, each output of one group of said output means providing a sequence of correction signals at a separate frequency which is a dividend of the frequency of the input pulses to said counter device, each output of a second group of said output means providing a gating voltage level for an interval spanning selected numbers of said input pulses, gate means responsive to application of gating voltage levels from said second group of output means to transmit a sequence of correction signals from said first group of output means at frequencies which vary in accordance with a pre-selected program controlled by said second group of said output means, and mean to add the sequence of correction signals from said gate means to the sequence of counting pulses from said detector means to generate a corrected count which is totaled in said first counter device.

8. Apparatus according to claim 7 wherein said gate means includes a series of individual gate elements, each element being connected to one output means of each of said two groups, the outputs of said gate elements being connected to said adding means, said adding means including an element to shape the correction signals from said gate outputs into individual correction pulses similar to the pulses in said sequence of counting pulses, and a delay circuit to avoid pulse coincidence so that individual correction pulses may be added to said sequence of counting pulses in intervals between the counting pulses in said sequence.

9. Apparatus according to claim 8 wherein said second counter device includes switching circuitry connected to said second group of outputs to provide gating voltage levels which operate in sequence to turn on the individual gate elements of said gate means.

10. Apparatus according to claim 7 including feedback means to stabilize and maintain the gating voltage level at the final output of said second group when the count in said second counter device reaches a selected count.

11. Apparatus according to claim 7 wherein said display counter device comprising a digital display providing a digital read-out of the count, as corrected by the addition of correction signals.

12. Apparatus according to claim 7 wherein said counter devices comprise counter chains responsive to negative-going pulse edges to generate digital output signals.

13. Counting apparatus for adding counts to the count indicated by a train of counting pulses comprising: a first counting means for coupling to a source of counting pulses and having an output for connection to count-responsive utilization means, second counting means having a plurality of stages and having an input for connection to the source of counting pulses, a plurality of first output means each connected to one of said counter stages for providing pulse outputs at different pulse output repetition rates in response to a train of counting pulses, gating means coupled to each of said first output means for selectively providing one of said pulse outputs at an output of said gating means, further outputs in said second counting means interconnected such that each of said further outputs provides an indication of a count interval spanning selected numbers of counting pulses, said further outputs each being connected to said gating means for selective gating to couple one of said first output means to the output of said gating means, said means adding pulses provided from said output of said gating means to the input of said first counter means, whereby a predetermined correction is made to a count represented by the train of counting pulses in response to the magnitude of the count.

14. Apparatus according to claim 13 wherein said stages of said second counting means connected to said plurality of first output means comprise means for dividing said train of counting pulses.

15. A method for correcting the read-out of an electronic detecting device providing a sequence of counting pulses indicative of the count detected by said detecting device, to compensate for errors introduced by missed counts due to coincidence of particles detected by said device, comprising the steps of providing said counting pulses to both first and second counting means, producing in said second counting means a plurality of pulse trains of differing frequency in response to said counting pulses, selecting one of said pulse trains in correspondence with a selected interval spanning a selected number of consecutive counting pulses to provide a selected pulse train, and adding the selected pulse train to said counting pulses provided to said first counting means.

16. The method of claim 15 wherein the step of selecting comprises providing said pulse trains to gating means, producing in sequence gating outputs from said second counting means, each gating output being produced during one of the intervals spanning selected members of said counting pulses, and applying the gating outputs of said gating means for providing a selected pulse train from said gating means for addition to said counting pulses.

* * * * *